United States Patent
Echigo et al.

(12) 
(10) Patent No.: US 6,184,014 B1
(45) Date of Patent: Feb. 6, 2001

(54) BACTERIAL POLYPHENOL OXIDASE FROM BACILLUS FOR USE IN OXIDATION OF COLORED SUBSTANCES

(75) Inventors: Takashi Echigo, Ichihara; Ritsuko Ohno, Funabashi, both of (JP)

(73) Assignee: Novo Nordisk A/S, Bagsvaerd (DK)

( * ) Notice: Under 35 U.S.C. 154(b), the term of this patent shall be extended for 0 days.

(21) Appl. No.: 09/110,960

(22) Filed: Jul. 7, 1998

Related U.S. Application Data

(63) Continuation of application No. PCT/DK97/00038, filed on Jan. 29, 1997.

(30) Foreign Application Priority Data

Jan. 29, 1996 (JP) .................................................. 8-012977

(51) Int. Cl.$^7$ .................................................. A61K 38/44
(52) U.S. Cl. .................... 435/189; 424/94.4; 435/252.5; 435/264
(58) Field of Search .......................... 424/94.4; 435/189, 435/252.5, 264

(56) References Cited

U.S. PATENT DOCUMENTS 5,356,437   10/1994   Pedersen et al. ........................ 8/401

FOREIGN PATENT DOCUMENTS

WO 91/05839   5/1991   (WO) .
WO 93/23600   11/1993  (WO) .

OTHER PUBLICATIONS

Pradhan et al., Environment & Ecology 8(2):643–645 (1990).*
Dialog Information Services, File 34: SciSearch, Dialog Accession No. 13790482, 1995.
Dialog Information Services, File 34: SciSearch, Dialog Accession No. 11729180, 1992.
Dialog Information Services, File 5, Biosis Previews, Dialog Accession No. 5933285, Biosis No. 84065850, 1987.
Dialog Information Services, File 5, Biosis Previews, Dialog Accession No. 6425522, Biosis No. 85026043, 1987.
National Library of Medicine (NLM), File Medline, Medline Accession No. 86082261, 1985.
Dialog Information Services, File 5, Biosis Previews, Dialog Accession No. 11584875, Biosis No. 98184875, 1995.
Dialog Information Services, File 5, Biosis Previews, Dialog Accession No. 7184416, Biosis No. 88107161, 1989.

* cited by examiner

*Primary Examiner*—Jean C. Witz
(74) *Attorney, Agent, or Firm*—Steve T. Zelson, Esq.; Reza Green, Esq.

(57) ABSTRACT

The present invention provides polyphenol oxidases from bacteria, particularly from the genus Bacillus including, without limitation, B. licheniformis, B. natto, and B. sphaericus, In some embodiments, the polyphenol oxidase has an optimum reaction pH of about 7; an optimum reaction temperature between 60° C. and 80° C.; and a molecular weight of 51,000 measured by gel filtration chromatography. The enzymes of the invention are useful for oxidizing and/or bleaching a variety of substrates.

17 Claims, 2 Drawing Sheets

BACTERIAL POLYPHENOL OXIDASE FROM BACILLUS FOR USE IN OXIDATION OF COLORED SUBSTANCES

CROSS-REFERENCE TO RELATED APPLICATIONS

This application is a continuation of PCT/DK97/00038 filed on Jan. 29, 1997 and claims priority under 35 U.S.C. 119 of Japanese application Ser. No. 8/12977 filed Jan. 29, 1996, the contents of which are fully incorporated herein by reference.

TECHNICAL FIELD

The present invention relates to a bacterial polyphenol oxidase, to a process of making the enzyme, to a bacterial strain that produces the enzyme, and to processes using the enzyme. More specifically, the present invention provides a novel enzyme source of polyphenol oxidase for use in the oxidation of colored substances and oxidation of polyphenol-containing substances and also for use in cleaning.

BACKGROUND ART

Polyphenol oxidase and laccase are known as enzymes that oxidize polyphenols. Various studies have been made on the use of polyphenol-oxidizing enzymes. For example, WO 94-29510 reports the delignination in the field of paper and pulp; and WO 91-05839, EP 91619032, DE 4008894 and JP-A 64-60693 report the use of the enzymes for bleaching in laundry washing.

However, the only known microbial sources for polyphenol oxidase and laccabe are mold fungi such as Basidiomycetes and Deuteromycetes., and it is generally difficult to cultivate large amounts of such fungi and, in addition, the rate of growth of the cells during cultivation is not high. Improving the enzyme yield by mutation or by use of genetic engineering technology is more difficult with these fungi than with bacteria, since the fungi have complicated life cycles and have complicated gene structures comprising introns, etc. For these reasons, it is difficult to stably and inexpensively obtain large amounts of polyphenol oxidases from such fungi, and bacteria-derived polyphenol oxidases are desired in order to apply them to practical use.

It is the object of the present invention to provide a polyphenol oxidase to be produced by bacteria, the bacteria that produce the enzyme and the use of the enzyme, thus providing a novel enzyme source of polyphenol oxidase for use in the oxidation of colored substances and oxidation of polyphenol-containing substances and also for use in cleaning.

STATEMENT OF THE INVENTION

We, the present inventors have assiduously searched various bacteria for extracellular products that catalyze the oxidation of polyphenol substances. Though being extremely difficult, our search for such products has at last resulted in the finding of the fact that bacteria belonging to the genus Bacillus can extracellularly produce the intended enzyme. On the basis of this finding, we have completed the present invention.

Accordingly, the present invention provides the following:

A polyphenol oxidase which is derived from a bacterium.

A method for oxidizing a phenolic compound, an alkoxy group-containing aromatic compound, a halogenated phenolic compound or an aromatic amine compound, which comprises treating said compound with said polyphenol oxidase in the presence of oxygen.

A method for bleaching a colored substance, which comprises treating the colored substance with said polyphenol oxidase in the presence of oxygen.

A method for inhibiting the transfer of a textile dye from a dyed fabric to another fabric when said fabrics are washed together in a wash liquor, which method comprises treating the wash liquor with said polyphenol oxidase in the presence of oxygen.

A method for bleaching colored waste water, which comprises treating the colored waste water with said polyphenol oxidase in the presence of oxygen.

A method for inactivating a microorganism or virus, which comprises treating the microorganism or virus with said polyphenol oxidase in the presence of oxygen.

A method for bleaching of lignin-containing material, which comprises treating the lignin-containing material with said polyphenol oxidase in the presence of oxygen.

A detergent composition comprising said polyphenol oxidase.

A method for producing a polyphenol oxidase, which comprises cultivation of a polyphenol oxidase-producing bacterium of the genus Bacillus in a suitable nutrient medium, followed by recovery of the polyphenol oxidase.

Bacillus licheniformis strain SD3003 (FERM P-15383) which is productive of polyphenol oxidase.

Now, the present invention is described in detail hereinunder.

DETAILED DESCRIPTION OF THE INVENTION

Enzyme-producing Bacteria

According to the invention, polyphenol oxidase is derived from a bacterial strain, preferably a strain of the genus Bacillus. Any and every strain of the genus Bacillus having the ability to produce polyphenol oxidase can be used herein to obtain the polyphenol oxidase of the invention, and there is not any other specific; limitation on the bacteria to be used herein. The enzyme-producing bacteria employable herein include, for example, those of *Bacillus alcalophilus, Bacillus amyloliquefaciens, Bacillus brevis, Bacillus firmus, Bacillus licheniformis, Bacillus natto, Bacillus pumilus, Bacillus sphaericus, Bacillus subtilis,* etc. Some preferred species are *B. licheniformis, B. natto* and *B. sphaericus,* particularly *B. licheniformis.* Some preferred strains are Bacillus sp. NCIB 10314, *B. licheniformis* NCIB 8059, NCIB 8061, ATCC 6634, ATCC 9945a, ATCC 11945 and SD3003, *B. natto* SN AKU 0205 and *B. sphaericus* IFO 3341.

The strains NCIB 10314, NCIB 8059 and NCIB 8061 are freely available from National Collections of Industrial and Marine Bacteria Limited (NCIMB, previously NCIB), 23 St. Machar Drive, Aberdeen AB2 1RY, Scotland, United Kingdom.

The strains *B. licheniformis* ATCC 6634, ATCC 9945a and ATCC 11945 are freely available from American Type Culture Collection (ATCC), 12301 Parklawn Drive, Rockville, Md. 20852, United States of America.

The strain *B. natto* SN AKU 0205 is freely available from the culture collection of the Agricultural Faculty of Kyoto University, Kyoto, Japan.

The strain *B. sphaericus* IFO 3341 is freely available from the Institute for Fermentation (IFO), 17-85 Juso-honmachi 2-chome, Yodogawa-ku, Osaka 532, Japan.

The strain *B. licheniformis* SD3003 was deposited as FERM P-15383 on Dec. 28, 1995 at the National Institute of Bioscience and Human-Technology, Ministry of International Trade and Industry, 1-3 Higashi 1-chome, Tsukuba-shi, Ibaraki-ken 305, Japan. The deposit was subsequently transferred to an international deposit under the Budapest Treaty on Jan. 28, 1997 under the deposit number FERM BP-5801. The deposit was made by Showa Denko K. K., Japan, and is being assigned to Novo Nordisk A/S. The following results were found from morphological observations and physiological tests with this representative strain according to the invention:

| Property | Results |
| --- | --- |
| Morphology | rod shaped |
| Gram-staining Ability | + |
| Spores | + |
| Shape | Oval |
| Position | Central to Semi-peripheral |
| Sporangia | No Evagination |
| Motility | + |
| Behavior Toward Oxygen | Anaerobic to Aeration |
| Catalase | + |
| Growth in Anaerobic Condition | + |
| V-P Reaction | + |
| pH in V-P Broth | 5.2 |
| Production of Acid from Glucose | + |
| Production of Gas from Glucose | − |
| Liquefaction of Gelatin | + |
| Decomposition of Starch | + |
| Utilization of Citrate | + |
| Utilization of Propionate | + |
| Egg Yolk Reaction | − |
| Reduction of Nitrate | + |
| Growth at pH 6.8 (in nutrient broth) | + |
| Growth at pH 5.7 | + |
| Growth in the Presence of 5 NaCl | + |
| Growth in the Presence of 7 NaCl | + |
| Growth at 10° C. | − |
| Growth at 30° C. | + |
| Growth at 55° C. | + |
| Growth at 65° C. | − |
| GC content (mol %) of Intracellular DNA(*) | 46 |

(*)Measured through HPLC.

From the above-mentioned results and with reference to "Bergey's Manual of Systematic Bacteriology", Vol. 2, 1986, Williams & Wilkins, and "The Genus Bacillus", 1973, U.S. Department of Agriculture, this strain is classified as Bacillus licheniformis SD3003.

Preparation of Enzyme

The polyphenol oxidase of the present invention can be obtained by cultivating the cells of strains belonging to the genus Bacillus such as those mentioned hereinabove, or those of mutants thereof. In addition, it can also be obtained by cultivating transformants from such strains to be prepared through genetic engineering. For example, host cells as transformed with an expression vector to be prepared by inserting a DNA that codes for the polyphenol oxidase of the invention, along with suitable promoter, operator and terminator DNAs that function to make said enzyme-encoding DNA express the enzyme in host organisms, into a DNA vector having a replication-initiating point at which the replication of said vector in host organisms is initiated; or host cells as transformed through integration of a DNA that codes for the polyphenol oxidase of the invention with a DNA of a host cell along with suitable promoter, operator and terminator DNAs that function to make said enzyme-encoding DNA express the enzyme in host organisms are cultivated under the condition under which the intended polyphenol oxidase can be expressed, and the thus-expressed polyphenol oxidase is collected from the culture of the thus-cultivated transformant cells.

To obtain a DNA fragment that codes for the polyphenol oxidase of the invention, any ordinary methods are employable. For example, the cDNA or genome library extracted from the strains as referred to hereinabove may be used as the DNA sources. Using, as the probe, an oligonucleotide as synthesized on the basis of the amino acid sequence of the intended enzyme, polyphenol oxidase, of the invention, or on the basis of the amino acid sequence of a known polyphenol oxidase, the intended DNA fragment may be specifically identified. Apart from these, clones that express enzymatic activity may be selected, or clones capable of producing a protein that reacts with an antibody to the enzyme, polyphenol oxidase of the invention may be selected.

The polyphenol oxidase of the present invention can be obtained by cultivating the enzyme-producing cells on a conventional synthetic medium or nutrient medium comprising an organic carbon source and an organic nitrogen source. It is desirable to add to the medium a metal salt of $Cu^{2+}$ ion at a concentration of from 0.001 mM to 10 mM, preferably from 0.01 mM to 1 mM. It is also desirable to add thereto a metal salt of $Mn^{2+}$ ion at a Concentration of from 0.001 mM to 100 mM, preferably from 0.01 mM to 10 mM. The cultivation temperature may be from 20 to 60° C., preferably from 30 to 55° C. The cultivation time may be suitably from 20 hours to 200 hours, preferably from 46 hours to 150 hours.

The polyphenol oxidase as secreted by the cells can be recovered by any ordinary means. The means of recovering the enzyme may comprise a series of steps of separating the cells from the medium by centrifugation, filtration or membrane separation, followed by purifying the enzyme through chromatography such as ion-exchange chromatography or the like. Concentrating by use of an ultrafiltration membrane is also effective for the recovery of the enzyme. In addition, it is also possible to isolate and concentrate the enzyme through salting-out with ammonium sulfate or the like.

Properties of Enzyme

The polyphenyl oxidase of the invention preferably has one or more of the following properties: Optimum reaction pH about 7, optimum reaction temperature between 60° C. and 80° C., and a molecular weight of about 51,000 (as measured by GFC).

One typical example of the polyphenol oxidase of the present invention is the enzyme derived from *Bacillus licheniformis* SD3003, which catalyzes oxidation within a broad pH range of from 5 to 9, but preferably from 6 to 8, more preferably about pH 7 (see FIG. 1). Thus, this enzyme is characterized in that it catalyzes oxidation within a neutral pH range. The optimum temperature for the action of the enzyme may be from 60° C. to 80° C. (see FIG. 2). The activity after 30 minutes heat treatment at various predetermined temperatures at pH 7 shows a residual activity of almost 100 at 70° C. (FIG. 3). After the enzyme has been treated in a buffer having varying pH values at 30° C. for 30 minutes, its activity is still stable in a broad pH range (see FIG. 4). These results ensure the stable activity of the enzyme to catalyze oxidation in various solutions within a broad pH range that covers from weakly acidic to weakly alkaline, at medium to low temperatures. The enzyme was found to have a molecular weight of about 51,000 through GFC analysis.

The polyphenol oxidase of the present invention can be used in combination with any ordinary enzyme that has optimum reaction pH at acidic pH. A combination of a conventional polyphenol oxidase having optimum reaction pH in the acidic range and the polyphenol oxidase of the present invention may make it possible to effect polyphenol oxidase reaction within a broad pH range covering from acidic conditions to weakly alkaline conditions. For the combination of these enzymes for the intended object, the ratio of the activity amount of the polyphenol oxidase that is most active at acidic pH values to that of the polyphenol oxidase of the present invention to be mixed with the former may be preferably from 1/10 to 10/1 (on activity or enzyme protein basis), more preferably from 1/3 to 3/1. In order to attain the polyphenol oxidase reaction within such a broad pH range, the polyphenol oxidase of the present invention is useful.

Method of Measuring Enzyme Activity

To determine the polyphenol oxidase in the present invention, the enzyme was reacted with 20 ppm of syringaldazine in an aqueous solution comprising 100 mM Bis-Tris-HCl buffer (pH 7.0) (Bis-Tris is available from Dotite Reagent Co.) at 20° C., and the absorbance at 525 nm of the resulting reaction mixture was measured. The activity amount of the enzyme that oxidizes 1 nmol of syringaldazine per minute is defined herein as 1 munit (hereinafter referred to as mU). The polyphenol oxidase of the invention is generally used at a concentration of from 10 to 500 mU/ml in the treatment of polyphenol-containing substances.

Use of Enzyme for Bleaching

The polyphenol oxidase of the invention is useful for oxidizing various substrates, particularly phenolic compounds, and for bleaching various colored substances in the presence of oxygen, Thus, the polyphenol oxidase of the invention finds application for bleaching of dye in solutions.

The polyphenol oxidase of the invention also finds application for dye transfer inhibition, e.g. for treatment of dyed textiles (cf., e.g. WO 92/18687) or during laundering (cf. e.g. WO 91/05839).Thus, the polyphenol oxidase of the invention may be used for inhibiting the transfer of a textile dye from a dyed fabric to another fabric when said fabrics are washed together in a wash liquor, the method comprising treatment of the wash liquor with the polyphenol oxidase of the invention, optionally in the presence of an additional oxidisable substrate. The textile dye may be a synthetic dye such as an azo dye, or a natural or nature-identical dye.

The polyphenol oxidase of the present invention is useful in the field of cleaning and bleaching. Thus, the present invention provides the use of the bacteria-derived enzyme in said field. The use of polyphenol oxidases in bleaching is disclosed in, for example, WO 91-05839, DE 4008894 and JP-A 64-60693.

Oxidative bleaching with hydrogen peroxide is widely employed at present in cleaning and washing. However, the bleaching activity of hydrogen oxide is not satisfactory at low temperatures of 60° C. or lower. In order to overcome this problem, hydrogen peroxide is used along with peracid precursors. However, the bleaching activity of the combination is still not satisfactory at temperatures of 40° C. or lower. Therefore, more effective bleaching systems are desired.

The polyphenol oxidase of the present invention can be combined with one or more of conventional oxidizing agents that have heretofore been used for oxidative bleaching, such as air, oxygen, ozone, hydrogen peroxide, hydrogen peroxide precursors, peracid precursors and peracids, thereby promoting the oxidative bleaching with the enzyme. Thus, the enzyme of the present invention can be effectively combined with any conventional oxidizing agents to enhance its oxidizing and bleaching activity.

The polyphenol oxidase of the present invention can be combined with one or more substances having peroxidase activity, such as peroxidase, lignin peroxidase, manganese peroxidase, etc., thereby promoting the oxidative bleaching with these enzymes.

Of the above-mentioned oxidizing agents, hydrogen peroxide precursors are dissolved in water to generate perhydroxyl ions. These substances include, for example, monohydrated or tetra-hydrated perborates, percarbonates, perborax, sodium perpyrophosphate, perbenzoic acid, urea-$H_2O_2$ reaction products, melamine-$H_2O_2$ reaction products, citric acid perhydrate, etc. Of these, especially preferred are perborates and percarbonates. As the hydrogen peroxide precursor, it is also possible to employ a hydrogen peroxide generating system comprising oxidase and a substrate for the enzyme. Examples of the oxidase of this type include glucose oxidase, alcohol oxidase, glycerol oxidase, amine oxidase, amino acid oxidase, D-amino acid oxidase, aryl alcohol oxidase, aldehyde oxidase, galactose oxidase, sorbose oxidase, ureate oxidase, xanthine oxidase, cholesterol oxidase, etc. Of these, especially preferred are glucose oxidase and alcohol oxidase.

The peracid precursors usable in the present invention are reactive acyl group-containing organic compounds, carboxylates, carboxylic acid anhydrides, acetates, etc. These include, for example, TAED (tetraacetylethylenediamine), TAMD (tetraacetylmethylenediamine), TAGU (tetraacetylglycoluril), DADHT (diacetyldioxohexahydrotriazine), SNOBS (sodium nonanoyloxybenzenesulfonate), ISONOBS (sodium isononanoyloxybenzenesulfonate), succinic anhydride benzoic anhydride, phthalic anhydride, PAG (glucose pentaacetate), and xylose tetraacetate. Of these, preferred are TAED and SNOBS.

The peracidsusable in the present invention include, for example, DPDDA (diperoxydodecanedioic acid), diperoxyisophthalic acid, magnesium monoperoxyphthalate hexahydrate, and NAPPA (nonylamidoperoxyadipic acid).

For use of the present polyphenol oxidase as a bleaching composition, the addition of another oxidizable substrate (for the polyphenol oxidase of the invention) at the beginning or during the washing and/or rinsing process may enhance the bleaching effect of the polyphenol oxidase employed.

Additional oxidizable substrate

Examples of such oxidizable substrates are organic compounds such as phenolic compounds, e.g. p-hydroxybenzenesulfdnate. Other examples of phenolic compounds which may be used for the present purpose are those given in M. Kato and S. Shimizu, *Plant Cell Physiol.* 26(7), 1985, pp. 1291–1301 (cf. Table 1 in particular) or B. C. Saunders et al., *Peroxidase,* London,. 1964, p. 141 ff.

In WO 94/121621 other types of enhancing agents are disclosed which may be used for the present purpose, e.g. phenothiazines or phenoxazines or derivatives thereof such as 10-methylphenothiazine, 10-phenothiazine-propionic acid, N-hydroxysuccinimide-10-phenothiazine-propionate, 10-ethyl-4-phenothiazine-carboxylic acid, 10-ethylphenothiazine, 10-propyl-phenothiazine, 10-isopropylphenothiazine, methyl-10-phenothiazine-propionate, 10-phenylphenothiazine, 10-allylphenothiazine, 10-(3-(4-methyl-1-piperazinyl)propyl)phenothiazine, 10-(2-pyrrolidinoethyl)phenothiazine, promazine, 2-chloro-10-methylphenothiazine, 2-acetyl-10-methylphenothiazine or 10-methylphenoxazine.

In WO 96/110079 another group of enhancing agents are disclosed which may be used for the present purpose, e.g., acetosyringone, byringaldehyde, methylsyringate or syringic acid.

The amount of oxidizable substrate corresponds to a concentration in the wash liquor of between 0.1 $\mu$M and 100 $\mu$M.

Detergent composition

The polyphenol oxidase of the present invention can be used in cleaning together with various detergents, cleaners or surfactants. The combination of the enzyme with any of such substances provides cleaner compositions or detergent compositions comprising the polyphenol oxidase of the present invention. Typical examples of cleaners and detergents into which the enzyme of the invention can be combined are cleaner compositions and detergent compositions comprising from 10 to 50% by weight, relative to the weight of the composition, of a surfactant, from 0 to 50% by weight of a builder, from 1 to 50% by weight of an alkaline agent or inorganic electrolyte, from 0.1 to 10% by weight of at least one component selected from the group consisting of re-soiling inhibitors, enzymes, bleaching agents, fluorescent dyes, caking inhibitors and antioxidants.

The surfactants may be any ones that are generally added to cleaners and detergents such as soap, and include, for example, aliphatic sulfates, such as salts of linear or branched alkyl or alkenyl sulfates, salts of amide sulfates, salts of linear or branched alkyl or alkenyl ether sulfates with one or more components of ethylene oxide, propylene oxide and butylene oxide added thereto; aliphatic sulfonates, such as salts of alkyl sulfonates,, salts of amide sulfonates, salts of dialkyl sulfosuccinates, salts of various sulfonates with $\alpha$-olefins, vinylidene-type olefins or internal olefins; aromatic sulfonates such as salts of linear or branched alkyl-benzenesulfonates; salts or amides of linear or branched alkyl or alkenyl ether carboxylates with one or more components of ethylene oxide, propylene oxide Wand butylene oxide added thereto; salts or esters of $\alpha$-sulfo-fatty acids; amino acid-type surfactants; phosphate-type surfactants, such as acidic alkyl or alkenyl phosphates, salts of alkyl or alkenyl phosphates; sulfonate-type ampholytic surfactants; betaine-type ampholytic surfactants; linear or branched alkyl or alkenyl ethers or alcohols with one or more components of ethylene oxide, propylene oxide and butylene oxide added thereto; polyoxyethylene alkyl or alkenyl phenyl ethers, in which the alkyl or alkenyl moiety may be linear or branched, with one or more components of ethylene oxide, propylene oxide and butylene oxide added thereto; higher fatty acid alkanolamides or alkylene oxide adducts thereof; sucrose fatty acid esters; monoesters of fatty acids with glycerin; alkyl or alkenyl amine oxides; tetraalkylammonium-type cationic surfactants, etc. The counter ion for the anionic surfactants is preferably sodium ion or potassium ion. These surfactants can be used singly or as combined.

The builders, alkaline agents and inorganic electrolytes include, for example, phosphates, such as orthophosphates, pyrophosphates, tripolyphosphates, metaphosphates, hexametaphosphates, phytates; salts of phosphonic acids such as ethane-1,1-diphosphonic acid and its derivatives, ethanehydroxy-1,1,2-triphosphonic acid, ethane-1,2-dicarboxy-1,2-diphosphonic acid, methanehydroxyphosphonic acid; salts of phosphonocarboxylic acids such as 2-phosphonobutane-1,2-dicarboxylic acid, 1-phosphonobutane-2,3,4-tricarboxylic acid, $\alpha$-methylphosphonosuccinic acid; salts of amino acids such as aspartic acid, glutamic acid; aminopolyacetates, such as nitritotriacetates, ethylenediamine-tetraacetates, diethylenetriamine-pentaacetates; polyelectrolytes, such as polyacrylic acid, polyitaconic acid, polymaleic acid, maleic anhydride copolymers, salts of carboxymethyl cellulose; non-dissociating polymers, such as polyethylene glycol, polyvinyl alcohol; carboxymethylates of diglycolic acid,; oxydisuccinic acid, carboxymethyloxysuccinic acid, gluconic acid, citric acid, lactic acid, tartaric acid, sucrose, lactose or the like; carboxymethylates of pentaerythritol; carboxymethylates of gluconic acid; salts of organic acids such as benzene-polycarboxylic acids, oxalic acid, malic acid, oxydisuccinic acid, gluconic acid; aluminosilicates, such as zeolite; inorganic acids, for example, alkali metal salts of carbonates, sesquicarbonates, sulfates, metasilicates or the like; organic substances, such as starch, urea; inorganic substances, such as sodium chloride, bentonite; and even organic alkaline agents, such as triethanolamine, diethanolamine, monoethanolamine, triisopropanolamine.

As has been mentioned hereinabove, the detergent composition of the present invention comprises, as the constitutive components, a surfactant and the polyphenol oxidase of the invention. If desired, it may further contain any of ampholytic surfactants; bleaching agents, such as perborates, percarbonates; dyes; builders; re-soiling inhibitors, such as polyethylene glycol, polyvinyl alcohol, polyvinyl pyrrolidone, carboxymethyl cellulose; caking inhibitors; antioxidants; and various enzymes such as oxidases other than the enzyme of the invention, peioxidases, proteases, lipases, amylases, cellulases.

To incorporate enzymes into the detergent composition of the present intention, any and every method is employable. Preferably, the enzyme is added to the detergent composition in the form of a solution or a non-dusting granulate. Non-dusting granulates can be made, for example, by means of stationary granulation, extrusion granulation, granulation with fluidized beds, centrifugal granulation with fluidized beds and the like. However, the shapes of the enzymes to be added to the detergent composition should not be limited to those as shaped according to such means.

Treatment of paper and pulp

Accordingly, the polyphenol oxidase of the invention may be used in a method for bleaching of lignin-containing material, in particular bleaching of pulp for paper production, which method comprises treatment of the lignin or lignin containing material with the polyphenol oxidase enzyme in the presence of oxygen.

For the purpose of delignination and bleaching in pulp production, any of the bacterial strains of the present invention may by inoculated into the material of pulp at any desired step of pulping, thereby producing the polyphenol oxidase of the invention during the step, or a pure product of the enzyme of the present invention may be directly added to wood chips or roughly-beaten pulp. In such manners, the enzyme of the present invention is effectively utilized in the field of bio-pulping and bio-bleaching.

The bleaching of pulp for paper production may be performed in analogy with SE 88/0673 and U.S. Pat. No. 4,690,895. Optionally, the treatment may be carried out in the presence of an additional oxidisable substrate, as described above.

Waste Water Treatment

The polyphenol oxidase of the invention also finds application in treatment of waste water e.g. waste water from the chemical or pharmaceutical industry, from dye manufacturing, from dye-works, from the textile industry, or from pulp production (cf. e.g. U.S. Pat. No. 4,623,465, or JP-A-2-31887). Thus, the invention provides a method for treatment of waste water from dye manufacturing, from dye-works, from textile industry, or from pulp manufacturing, the method comprising treatment of the waste water with the polyphenol oxidase in the presence of oxygen.

The polyphenol oxidase of the present invention is useful for the treatment of drainage containing natural substances and artificial substances having polyphenols in their constitutive moieties. The polyphenol oxidase of the invention acts on natural substances of this type, such as flavonoids, xanthones, melamines and ether vegetable dyes, as well as lignin. In addition, the polyphenol oxidase also acts on various toxic AOX substrates, such as dichlorophenol, trichlorophenol, etc.

Optionally, the treatment may be carried out in the presence of an additional oxidisable substrate, as described above.

Other Industrial Applications of Enzyme

Further, the polyphenol oxidase of the invention finds application for lignin modification, e.g. in particle board production. Binders for producing wood composites such as fibre boards and particle boards can be made from polyphenol oxidase treated lignin (cf. U.S. Pat. No. 4,432,921). Accordingly, the invention provides a method for enzymatic polymerization and/or modification of lignin or lignin containing material, which method comprises treatment of the lignin or lignin containing material with thelpolyphenol oxidase in the presence of oxygen.

In addition, polyphenol oxidase of the present invention may be used in biosensors, which reflect the characteristics of the enzyme and are therefore useful for monitoring various aromatic compounds in aqueous solutions or organic solvents at pH falling within a weakly acidic to weakly alkaline range.

Further, since the polyphenol oxidase of the present invention generates active phenoxy radicals, it can be used for efficiently inactivating microorganisms and viruses at pH falling within a Weakly acidic to weakly alkaline range. Namely, in addition to the microbicidal activity of the polyphenol oxidase itself of the invention against substrates, the enzyme can exhibit much stronger microbicidal activity while enzymatically generating such active phenoxy radicals. Moreover, even when the substances as microbicidally processed with the enzyme, polyphenol oxidase of the present invention are then brought into contact with human bodies or are ingested by human beings, or even when they are released in the atmosphere, they are safe, since the substances are, after having been oxidized with the enzyme, converted into safe substances with little toxicity. Thus, the enzyme of the present invention is very useful, as exhibiting its microbicidal activity at any desired stage to convert the substances processed with it into non-toxic and safe substances.

In addition, the polyphenol oxidase of the present invention is also useful in polymer production where are used the phenoxy radicals and quinones to be derived from the enzyme.

Moreover, where the polyphenol oxidase of the present invention is used to oxidize substances comprising easily-oxidizable polyphenols, such as catechols, it attains both self-oxidation and enzymatic and catalytic oxidation of polyphenols. Thus, the use of the polyphenol oxidase of the present invention for this purpose is extremely effective for attaining efficient oxidation of such substances.

EXAMPLES

Now, some typical examples of the present invention are mentioned below, which demonstrate the invention more concretely. However, these are to merely exemplify some preferred embodiments of the invention but are not to restrict the scope of the invention.

Example 1

Cultivation, Crude Purification, Concentration

A 500-ml flask was used herein as the incubator. 100 ml of a medium comprising 0.134 $Na_2HPO_4.12-H_2O$, 0.03 $KH_2PO_4$, 1 maltose, 1 peptone, 0.1 yeast extract, 0.05 $MgSO_4.7-h_2O$, 0.1 mM $CuSO4$, 1 mM $MnCl_2$ and 2 mM $CaCl_2$ was prepared and adjusted to pH 7.8 with 20% $Na_2CO_3$ added thereto. Cells of Bacillus licheniformis SDB3003 (FERM P-15383) were inoculated on the medium, and incubated therein at 50° C. for 16 hours while shaking. Then, tihe temperature of the medium was lowered to 35° C., and the incubation was continued for further 3 days.

After the incubation, the culture was centrifuged at 4° C. to remove the cells. Ammonium sulfate fractionation was found to be effective for purifying and concentrating the resulting culture broth. More specifically, the culture broth was fractionated with ammonium sulfate at from 20 to 60% of saturation concentration, and most of the active polyphenol oxidase fraction was collected as the precipitate. The resulting precipitate thug collected through the ammonium sulfate fractionation was dialyzed against 10 mM Bis-Tris-HCl buffer (pH 7.0), and the resulting dialysate was purified and concentrated through ultrafiltration. Thus was obtained an aqueous, crudely-purified concentrate of the enzyme (800 mU/ml) in the fractions falling within A molecular weight range of from 10,000 to 100,000.

Example 2

Substrate Specificity

The aqueous, crudely-purified concentrate of the enzyme as obtained in the previous Example 1 was tested for the substrate specificity to the oxidation of polyphenol compounds. More specifically, thy enzyme concentrate was added to 0.05 mM of each substrate shown in Table 1 below, in 100 mM of Bis-Tris-HCl buffer (pH 7.0) at room temperature (20° C.). The difference in the oxygen consumption between the test sample comprising the enzyme concentrate and the control sample not comprising it was determined. The results obtained are shown in the following Table.

| Substrate | Oxidation |
| --- | --- |
| Syringaldazine | + |
| 4-Anisidine | + |
| O-phenylenediamine | + |
| Ferulic Acid | + |

Example 3

Molecular Weight

The molecular weight of the enzyme prepared above was determined by GFC (gel filtration chromatography).

The aqueous, crudely-purified concentrate of the enzyme obtained in Example 1 was analyzed and fractionated by HPLC using a series of two GFC columns (Shodex PROTEIN KW-802.5) equilibrated with 1.34 $Na_2PO_4.12-H_2$(, 0.3 $KH_2PO_4$ and 1 NaCl at a flow rate of 1.0 ml/min using a UV detector (at 280 nm), and the activity of the fractionated enzyme was measured. As a result, the polyphenol oxidase activity peak was eluted within a molecular weight range of from 46,000 to 56,000. MW-Marker (HPLC) produced by Oriental Industrial Co. was used as molecular weight marker protein.

Example 4

Incubation in 5-Liter Incubator, Concentration, Crudle Purification

Three liters of a medium comprising 0.134 $Na_2HPO_4.12-H_2O$, 0.03 $KH_2PO_4$, 1 maltose, 1 peptone, 0.1 yeast extract, 0.5 $MgSO_{4.7}-H_2O$, 0.1 mM $CuSO_4$, 1 mM $MnClz_2$ and 2 mM $CaCl_2$ was prepared and adjusted to pH 7.8 with 10 NaOH. This was put into a 5-liter incubator. Cells of *Bacillus licheniformis* SD3003 (FERM P-15383) were inoculated on the medium, and incubated therein at 50° C. for 16 hours while shaking. Then, the temperature of the medium was lowered to 35° C., and the incubation was continued for further 3 days. After the incubation, tie culture was centrifuged at 4° C. to obtain a cell-free culture broth.

Next, a part of this culture broth was fractionated in a mini-tank ultrafiltration system (produced by Millipore Co.) using a mini-tank filter packet (Catalogue No.: PTGCOMP04, produced by Millipore Co.) to obtain a fraction having a molecular weight of 10,000 or higher, which was then concentrated. The resulting concentrate was dialyzed against 200 ppm $NH_4HCO_3$, and then lyophilized to obtain a crudely-purified, dry lyophilisate. The polyphenol oxidase activity of the dry lyophilisate was 500 mU/mg.

Example 5

Washing of Soiled Fabric with Enzyme-containing Detergent 0.1 g of the dry lyophilisate as obtained in Example 4 was added to 10 g of a standard detergent comprising 25 by weight of sodium linear alkylbenzenesulfonate (LAS), 5 by weight of polyoxyethylene lauryl ether, 15 by weight of sodium tripolyphosphate, 6 by weight of sodium silicate, 1 by weight of sodium carboxymethyl cellulose and 48 by weight of $Na_2SO_4$, to prepare an enzyme-containing detergent sample. The detergent not containing the enzyme was referred to as a control detergent sample.

0.2 ml of 100 ppm Evans' Blue (commercially-available from Wako Pure Chemical Industry Co.) was applied onto the center of white cotton cloths (5 cm×5 cm) to prepare soiled swatches.

One soiled swatch was put into a 500-ml beaker along with 10 ml of water, 10 mg of either the enzyme-containing detergent sample of the control detergent sample with no enzyme. Then, the beaker was shaken for 12 minutes to wash the cloth. After thus having been washed, the swatch was rinsed with water and dried in air, and its color was measured with a color-difference meter (CR-200, produced by Minolta Co.) to determine the Y, y and x values of the cloth. From these, the Z value thereof was obtained according to the equation, $Z=(1-x-y)Y/y$.

The results demonstrated an increase of 1.5 points in the degree of whiteness of the swatch treated with the enzyme-containing detergent sample, compared with that treated with the control detergent sample with no enzyme.

Example 6

Plate test for polyphenol oxidase in various strains

The following strains were tested: *B. licheniformis* NCIB 8059, NCIB 8061, ATCC 6634, ATCC 9945a, ATCC 11945 and SD3003 and *B. natto* SN AKU 0205.

Each strain was cultivated for 3 days with shaking at 34° C. in a medium of the following composition at pH 8.6: 0.5 malic acid, 0.5 peptone, 0.05 $MgSO_4. 7H_2O$, 0.01 mM $CUSO_4$, 0.05 mM $MnCl_2$, 0.1 mM $CaCl_2$.

Each culture broth was tested in a plate assay, using plates with the following composition: 50 mM buffer (neutral pH), 100 ppm $MgSO_4. 7H_2O$, 1.8 agar and 25 ppm syringaldazine as an indicator. The culture broth was applied to a paper disk settled on the plate.

For each of the above strains, a distinct pink zone was observed around the paper disk indicating the presence of polyphenol oxidase activity.

Example 7

Assay of polyphenol oxidase for various strains

A well of a 96-well micro-titer dish was filled with 20 μl buffer (1 M, pH 7.1), 160 μl water, 20 μl supernatant of culture broth prepared as in the previous example using the strains shown below, and 20 μl syringaldazine solution (200 ppm in 50 ethanol). This was incubated for 5 hours at room temperature, and the absorbance at 550 nm was measured before and after the incubation. The results are shown as the increase in absorbance for each strain:

| Strain | Increase of absorbance |
| --- | --- |
| IFO 3341 | .002 |
| NCIB 10314 | .004 |
| NCIB 8059 | .023 |
| NCIB 8061 | .010 |
| ATCC 6634 | .024 |
| ATCC 9945a | .052 |
| ATCC 11945 | .047 |

These results confirm a positive polyphenol oxidase activity for the Bacillus strains.

ADVANTAGES OF THE INVENTION

As has been described in detail hereinabove, the present invention provides a polyphenol oxidase produced by bacteria. It has been found that this enzyme attains enzymatic oxidation and can be used for oxidative treatment of polyphenol substances and colored substances and can be used for the purpose of cleaning and bleaching.

According to the method of the present invention, the polyphenol oxidase of the invention can be produced highly efficiently.

*Bacillus licheniformis* SD3003 of the invention is effectively used for the production of the polyphenol oxidase of the invention.

The present invention also provides a method of using the enzyme, polyphenol oxidase of the invention for processing colored substances, for processing paper, pulp and fibers, for bleaching and cleaning various substances, and for processing microorganisms and viruses to make them non-toxic

Figure 1:
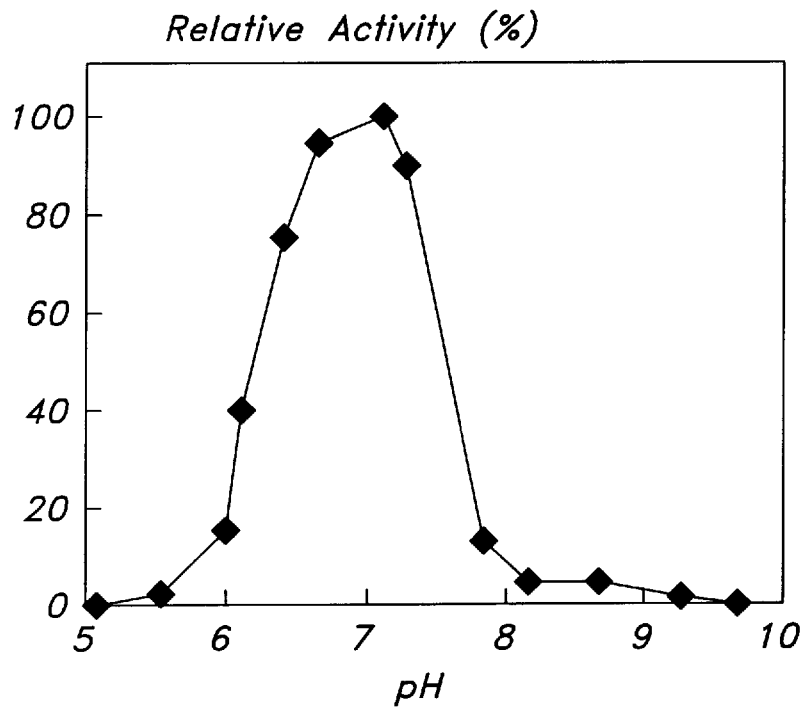
FIG. 1 shows a pH profile for DS 3003-derived polyphenol oxidase.
Figure 2:
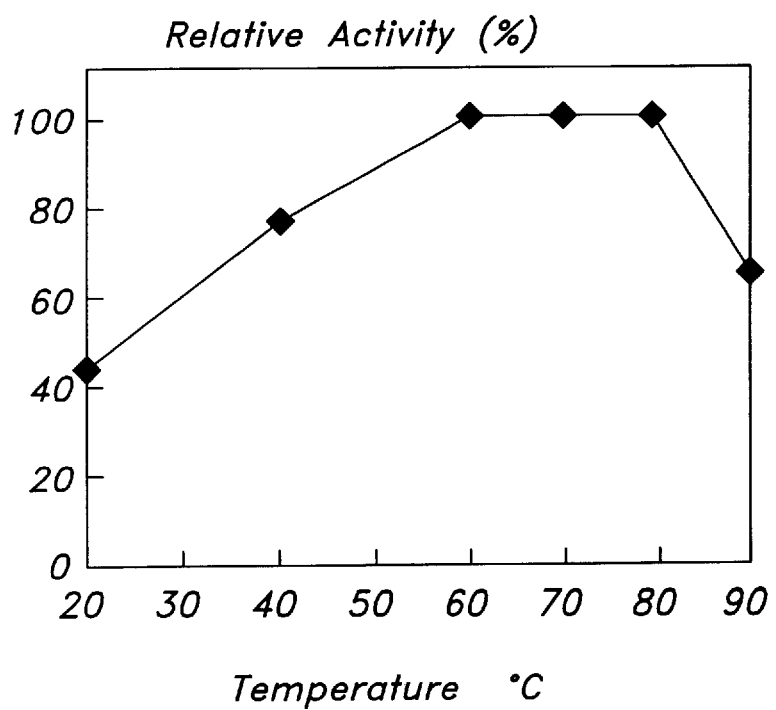
FIG. 2 shows a temperature profile for DS 3003-derived polyphenol oxidase.
Figure 3:
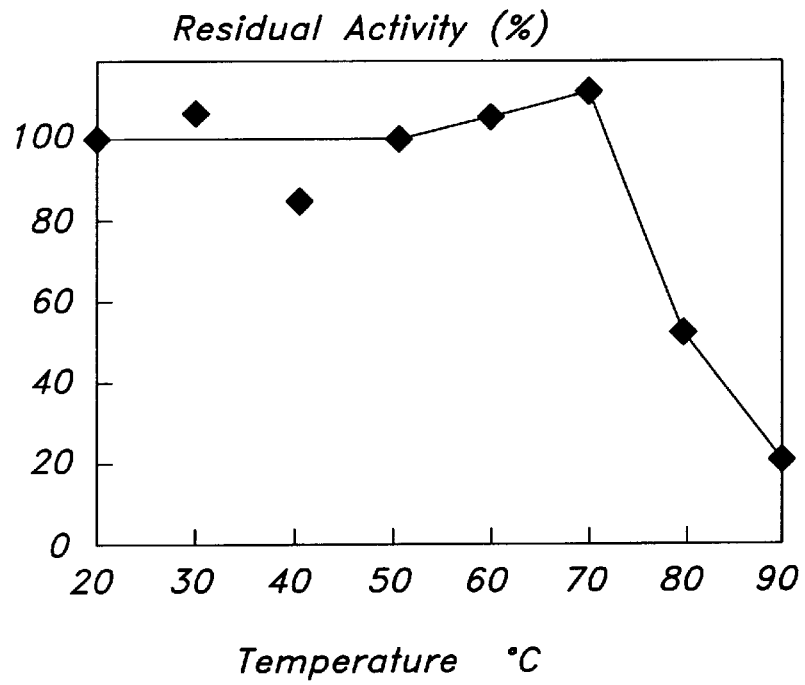
FIG. 3 snows a graph showing the temperature-dependent stability of DS3003-derived polyphenol oxidase.
Figure 4:
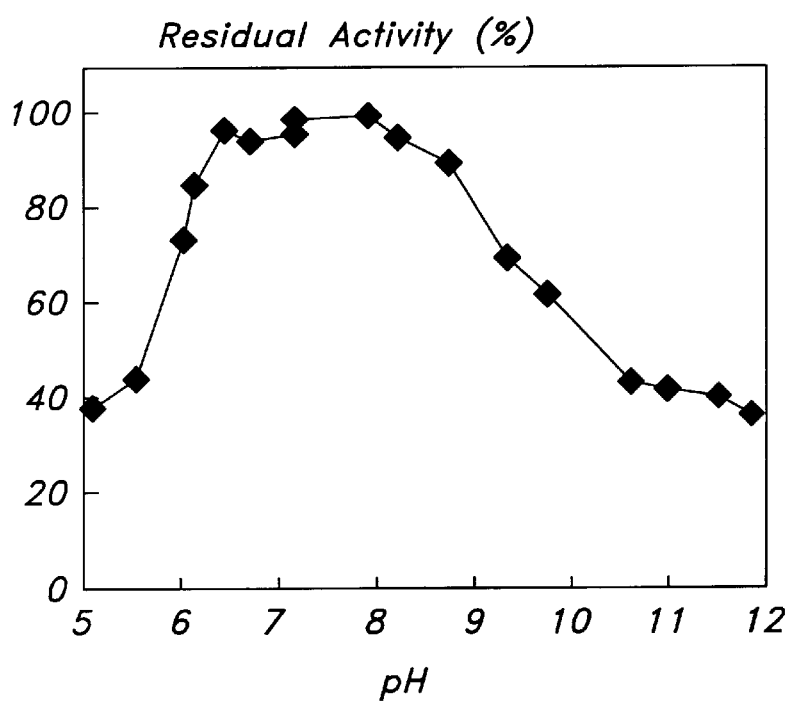
FIG. 4 shows a graph showing the pH-dependent stability of DS 3003-derived polyphenol oxidase.

What is claimed is:

1. A purified polyphenol oxidase derived from a bacterium of the genus Bacillus, wherein said bacterium is a strain of *B. licheniformis, B. natto* or *B. sphaericus*.

2. The polyphenol oxidase of claim 1, which is obtainable from Bacillus sp. NCIB 10314, *B. licheniformis* NCIB 8059, NCIB 8061, ATCC 6634, ATCC 9945a, ATCC 11945 or SD3003 FERM BP-5801, *B. natto* SN AKU 0205 or *B. sphaericus* IFb 3341.

3. The polyphenol oxidase of claim 1, which is obtainable from *B. licheniformis* SD3003 FERM BP-5801.

4. The polyphenol oxidase of claim 1, which has the following characteristics:

Optimum reaction pH of about 7,

Optimum reaction temperature between 60° C. and 80° C.,

Molecular weight of about 51,000 (by gel filtration chromatography).

5. A method for oxidizing a phenolic compound, an alkoxy group-containing aromatic compound, a halogenated phenolic compound or an aromatic amine compound, which comprises treating said compound with the polyphenol oxidase of claim 1 in the presence of oxygen.

6. A method for bleaching a colored substance, which comprises treating the colored substance with the polyphenol oxidase of claim 1 in the presence of oxygen.

7. A method for inhibiting the transfer of a textile dye from a dyed fabric to another fabric when said fabrics are washed together in a wash liquor, which method comprises treating the wash liquor with the polyphenol oxidase of any of claim 1 in the presence of oxygen.

8. A method for bleaching colored waste water, which comprises treating the colored waste water with the polyphenol oxidase of claim 1 in the presence of oxygen.

9. A method for inactivating a microorganism or virus, which comprises treating the microorganism or virus with the polyphenol oxidase of claim 1 in the presence of oxygen.

10. A method for bleaching of lignin-containing material, which comprises treating the lignin-containing material with the polyphenol oxidase of claim 1 in the presence of oxygen.

11. The method of claim 5, wherein the polyphenol oxidase is used together with an additional oxidizable substrate.

12. The method of claim 5, wherein the polyphenol oxidase is used together with a substance having peroxidase activity.

13. The method of claim 5, wherein the polyphenol oxidase is used together with an oxidase and a substrate for the oxidase.

14. A detergent composition comprising the polyphenol oxidase of claim 1.

15. A method for producing a polyphenol oxidase of claim 1, which comprises cultivation of a strain of *B. licheniformis, B. natto* or *B. sphaericus* in a suitable nutrient medium, followed by recovery of the polyphenol oxidase.

16. The method of claim 1, wherein the bacterium is *B. licheniformis* NCIB 8059, NCIB 8061, ATCC 6634, ATCC 9945a, ATCC 11945 and SD3003 (FERM BP-5801), *B. natto* SN AKU 0205, *B. sphaericus* IFO 3341 or a mutant of any of these.

17. An isolated *Bacillus licheniformis* strain SD3003 (FERM BP-5801).

* * * * *